United States Patent [19]

Winter et al.

[11] Patent Number: 5,079,166

[45] Date of Patent: Jan. 7, 1992

[54] MICROBIAL DEGRADATION OF TRICHLOROETHYLENE

[75] Inventors: Robert B. Winter, Woodland Hills; Kwang-Mu Yen; Burt D. Ensley, both of Thousand Oaks, all of Calif.

[73] Assignee: Amgen Inc., Thousand Oaks, Calif.

[21] Appl. No.: 235,354

[22] Filed: Oct. 19, 1988

Related U.S. Application Data

[63] Continuation-in-part of Ser. No. 177,640, Apr. 5, 1988, abandoned.

[51] Int. Cl.$^5$ .................... C07C 1/26; C12N 15/00; C12N 1/21; C12N 9/02; C12N 1/00; C02F 3/00; D06M 16/00
[52] U.S. Cl. .................... 435/262; 435/172.3; 435/252.3; 435/252.33; 435/252.34; 435/264; 435/189; 435/320.1; 435/874; 210/601; 935/59
[58] Field of Search ................ 435/121, 172.3, 252.34, 435/253.3, 262, 320, 874, 877, 264, 252.33, 189; 935/14, 29, 56, 72, 59; 210/601

[56] References Cited

U.S. PATENT DOCUMENTS 4,477,570  10/1984  Colaruotolo et al. .............. 435/253
4,520,103  5/1985  Ensley ............................. 435/121

OTHER PUBLICATIONS

Whitee, G. M. et al., Meeting for Am. Society for Microbiology, Mar. 3-7, 1985, Abstract Annu. Meeting.
Nelson et al., Appl. Environ. Micro., vol. 53, pp. 949-954 (1987).
Subramanian, V. et al., J. Biol. Chem., vol. 256, pp. 2723-2730 (1981).
Whitee, G. M., (1986) PhD. Thesis at The Univ. of Texas at Austin, Dissertation Abstracts International, p. 1861, vol. 47/05-B.

*Primary Examiner*—Richard A. Schwartz
*Assistant Examiner*—Joan Ellis
*Attorney, Agent, or Firm*—Allegretti and Witcoff

[57] ABSTRACT

This invention relates to a method for the microbial degradation of trichlorethylene by treating trichloroethylene with *Pseudomonas mendocina* KR-1 or *Pseudomonas putida* Y2101 or a microorganism host cell that contains a recombinant plasmid. The recombinant plasmid contains toluene monooxygenase genes from *Pseudomonas mendocina* KR-1. The microogranism host cell containing the recombinant plasmid must have been treated with an inducer of the toluene monooxygenase genes. The method may be applied to the treatment of loci of trichloroethylene chemical waste in water or soil. More particularly, the method may be applied to degrade trichloroethylene as it may be present as a pollutant or contaminant in water, in industrial effluents, in various land areas such as industrial sites, or in various laboratory or commercial installations.

15 Claims, 8 Drawing Sheets

MICROBIAL DEGRADATION OF TRICHLOROETHYLENE

This is a continuation-in-part of U.S. patent application Ser. No. 177,640, filed Apr. 5, 1988 now abandoned.

BACKGROUND

I. Field Of The Invention

This invention relates to an improved method for the microbial degradation of trichloroethylene by *Pseudomonas mendocina* KR-1 (PmKR1) or *Pseudomonas putida* KT2440 containing the pAUT1 plasmid from PmKR1 (Pp Y2101) or by genetically-engineered microorganisms containing the PmKR1 toluene monooxygenase genes. It has now been unexpectedly found that the PmKR1 toluene monooxygenase enzyme system is useful in the degradation of trichloroethylene. The isolation and cloning of gene segments encoding the toluene monooxygenase enzyme system of PmKR1 is described in U.S. patent application Ser. No. 177,631, filed Apr. 5, 1988, which is hereby incorporated by reference.

In one aspect, the present invention relates to a method for the microbial degradation of trichloroethylene by treating trichloroethylene with a microorganism host cell containing a recombinant plasmid, the recombinant plasmid containing the PmKR1 toluene monooxygenase genes. The microorganism host cell containing the recombinant plasmid must be treated with an inducer of the toluene monoxygenase genes in order to degrade trichloroethylene. The present invention provides a novel method of degrading trichloroethylene by providing genetically engineered microorganisms that exhibit levels of toluene monooxygenase enzyme activity under certain cell culture and assay conditions that exceed levels expressed in wildtype PmKR1 cells. The present invention therefore provides a more efficient means of conducting certain biodegradations dependent on this enzyme system, particularly the degradation of trichloroethylene. The invention is applicable for degrading trichloroethylene as it may be present as a pollutant or contaminant in open or closed environmental systems.

Trichloroethylene (TCE) is a widely used industrial solvent that is found frequently as a contaminant in groundwater, drinking water and waste water. Groundwater is the major reservoir of improperly treated hazardous wastes. More than 200 organic and inorganic chemicals have been identified in various groundwater supplies, however, of all such identified contaminating chemicals, the EPA has identified TCE as the most frequently observed chemical contaminant at National Priority List (NPL) sites in the United States.

The magnitude of the problem of groundwater contamination is further exemplified by the fact that ground water supplies 25% of all water used in the United States. Calculations by The Conservation Foundation ("Groundwater - Saving the Unseen Resource," November, 1985 at p. 5) show that in the United States, groundwater is the source of: (1) 35% of all municipal water, (2) 50% of all drinking water (97% in rural areas), (3) 40% of all water used in agricultural irrigation, and (4) 26% of all water used by industry (excluding electric power plants). Thus, the importance of developing environmentally effective techniques for the degradation of TCE into innocuous materials cannot be overemphasized.

Development of genetically engineered microorganisms which have superior abilities to degrade specific chemical contaminants, such as TCE, to innocuous materials is one important strategy in the development of cost effective and environmentally sound methods for hazardous chemical work cleanup. The development and use of microorganism host cells with recombinant plasmids containing PmKR1 toluene monooxygenase genes in the present invention is the first method employing such genetically engineered microorganisms useful for TCE chemical waste cleanup. The development and use of microorganism host cells containing the recombinant plasmids described herein are particularly advantageous because specific and well-characterized gene segments encoding PmKR1 toluene monooxygenase genes been cloned and used to construct the recombinant plasmids, as described in the above referenced U.S. patent application Ser. No 177,631. It is these gene segments placed under the regulation of certain promoters which specifically confer superior abilities to degrade TCE upon certain microorganism host cells used in this invention. This system readily permits manipulation of the isolated genes by cloning into a variety of cloning vectors and expression via a variety of different promoter systems, so as to increase and optimize metabolic activity to degrade TCE. In addition, this system readily permits the study and manipulation of the specific enzymes and proteins involved in TCE degradation. As a consequence of the preparation of DNA segments containing PmKR1 toluene monooxygenase genes, the incorporation of such DNA segments into suitable plasmid vectors and the transformation of microorganism host cells, PmKR1 toluene monooxygenase enzyme products are expressed and may be isolated. Thus, a different approach to the degradation of TCE may be taken using isolated and purified enzyme products, rather than the transformed microorganism host cells. It is contemplated that the PmKR1 toluene monooxygenase enzyme products could be used directly to degrade TCE. Such enzyme products could be released into or applied to loci of TCE chemical waste and could be useful in pollution control, for example, in the treatment of industrial waste water contaminated with TCE.

II. Description of the Art

Many different methods have been proposed for rendering toxic wastes innocuous. Among these are incineration, chemical transformation, and microbiological degradation. Because microbiological degradation of toxic waste does not involve the use of chemical reagents which might themselves be toxic and does not result in the production of large amounts of noxious fumes, such as produced in the incineration of toxic waste, it has become a preferred method of disposing of toxic waste.

Most microbiological degradations of toxic materials are based upon discovering a particular microorganism which will metabolize the toxic material, converting it to innocuous metabolic products, usually, in the case of toxic organic compounds, converting such compounds into carbon dioxide, water and salts. Finding microorganisms, in particular, genetically engineering microorganisms which can efficiently and safely convert toxic wastes into innocuous metabolic products is a highly complex procedure involving many arduous steps and requiring a significant expenditure of time. Most efforts thus far have focused on finding microorganisms indigenous to and isolated from contaminated soil or water.

One approach is to obtain a soil or water sample and enrich the sample for a mixture of microorganisms or isolate from a mixture a purified culture of a microorganism with the ability to degrade one or more toxic compounds. Several studies using mixtures of microorganisms containing methane-utilizating bacteria obtained by methane enrichment of a soil sample have shown that such mixtures have the ability to degrade TCE and other chlorinated ethenes. Fogel et al., Appl. Environ. Microbiol. 51: 720–724 (1986); Wilson and Wilson, Appl. Environ. Microbiol. 49: 242–243 (1985). Although these methane-utilizing cultures contain more than one type of bacterium, it is proposed that the methanotrophs are responsible for the degradation of TCE. Fogel et al. (supra) report a rate of TCE degradation of 0.03 nanomoles of TCE per minute per milligram of cell protein.

Other studies have not used mixtures of microorganisms but purified strains isolated from soil or water. One such approach is described in U.S. Pat. No. 4,493,895, wherein is claimed a process of microbial degradation of contaminating halogenated aromatic compounds into innocuous materials. This process comprises the steps of (1) collecting a sample of material from the site contaminated with obnoxious chemicals; (2) enriching the microorganisms found living in the sample; (3) separating the strains of microorganisms capable of having different metabolisms for the various chemicals in the sample from the site, from each other; (4) purifying the strains which are capable of biodegrading the chemicals to be disposed of; (5) applying the strain to the locus of the contaminants to be disposed of; and (6) monitoring of removal of the contaminants at the locus of the application. U.S. Pat. No. 4,477,570 describes and claims the microorganisms used in the above-described claimed process of U.S. Pat. No. 4,493,895.

Another approach is described in U.S. Pat. No. 4,664,805, wherein is claimed a process for decontaminating environments with halogenated organic compounds utilizing (1) microorganisms indigenous to the environment to be decontaminated which can metabolize but cannot grow on the contaminant; (2) a inoculum of microorganisms not indigenous to the environment which metabolize the contaminant faster than the indigenous microorganisms but cannot grow on it; and (3) a non-toxic analog of the contaminant which serves as a substrate for growth of the indigenous and non-indigenous microorganisms. Reliance is placed on microorganisms already present in the environment, so-called indigenous microorganisms to accomplish the degradation. The degradation is enhanced by the non-indigenous microorganism.

Yet another approach described in U.S. Pat. No. 4,511,657 involves a process of treating chemical waste landfill leachates with activated sludge containing bacteria capable of metabolizing obnoxious organics present in the leachates. All of the above described approaches involve the use of microorganisms which are indigenous to or isolated from contaminated soil or leachates. The degradative enzymes needed for microorganisms to degrade halogenated organic compounds may be encoded by genes borne on plasmids. A single plasmid generally contains genes encoding enzymes in a single degradative pathway. Plasmids have been employed in methods for the biodegradation of certain chlorinated aromatic organic compounds, as illustrated by U.S. Pat. No. 4,535,061 (which describes plasmid-assisted breeding procedures for generating pure and mixed cultures of microorganisms capable of dissimilating environmentally persistent chemical compounds) and U.S. Pat. No. 4,664,805 discussed above.

Using plasmids from microorganisms that degrade halogenated aromatic organic compounds (A.T.C.C. 31939-31945) (which microorganisms were described in U.S. Pat. Nos. 4,477,570 and 4,493,895) European Patent Application 8511008.1 discloses the preparation of hybrid plasmids and transconjugates containing these plasmids. European Patent Application 8511008.1 teaches a process for producing a microorganism having specificity for biodegrading halogenated organic compounds which comprises the steps of: (1) separately culturing and maintaining (a) a broad spectrum microorganism selected from the group of ATCC 31945 ATCC 31941, ATCC 31942, ATCC 31940, ATCC 31943, ATCC 31944, ATCC 31939 and mutants thereof, and (b) a broad host range vector; (2) separately isolating the plasmid-DNA from (a) and (b) above; (3) separately purifying the plasmid-DNA from (a) and (b) above; (4) separately enzymatically restricting the purified DNA from (a) and (b) above; (5) combining the products of step (4) and enzymatically ligating the combined products; (6) transforming the products of the ligation, into a receptive microorganism such as *E. coli* or species of Pseudomonas: (7) selecting those transformants having the desired plasmid-DNA inserted into the vector; (8) conjugating the selected plasmid-DNA into a receptive host selected from the group of *Pseudomonas, Klebsiella, Rhizobium, Agrobacterium, Escherichia* with aid of a helper plasmid; and (9) selecting those transconjugants having the desired plasmid DNA.

Eleven transconjugates were disclosed and unexpectedly a majority of the transconjugates were found to utilize as their sole carbon source certain aliphatic halogenated organic compounds, specifically, tetrachloroethylene, ethylene dichloride, methylchloroform and TCE, whereas the progenitor microorganisms A.T.C.C. 31939-31945 utilized only a broad spectrum of aromatic organic compounds as disclosed in U.S. Pat. No. 4,493,895. The only assay for utilization of these aliphatic halogenated organic compounds was growth on medium containing the compound where the growth was one-half greater than mean growth. Except for this growth assay, the transconjugates are completely uncharacterized. In particular, nothing is disclosed about the extent of degradation of these aliphatic halogenated organic compounds by these microorganisms or about the nature and toxicity of the metabolic products. Nothing is taught or disclosed regarding what genes, gene segments, enzymes, proteins or protein products are involved in the transconjugates' ability to metabolize such aliphatic halogenated organic compounds, including TCE. In particular, the teaching of European Patent Application 851008.1 is limited to utilization of aliphatic halogenated organic compounds, including TCE, by plasmids selected from the group of microorganisms designated as A.T.C.C. 31939-31945.

With respect to TCE metabolism specifically, partial degradation of TCE by anaerobic organisms has been reported but metabolites of the degradation process include vinyl chloride and dichloroethylene which are similarly harmful as groundwater contaminants. Kleopfer et al., *Environ. Sci. Technol.*, 19:277–280 (1985); Parsons et al., *J. Am. Water Works Assoc.*, 76:56–59 (1984); Vogel & McCarty, *Appl. Environ. Microbiol.*, 49:1080–1083 (1985). A recent report describes a naturally occurring bacterial isolate which is capable of degrading TCE under aerobic conditions. Nelson et al., *Appl. Environ. Microbiol.*, 52:383-384 (1986); Nelson et al., *Appl. Environ. Microbiol.*, 53:949-954 (1986). The microorganism designated Strain G4 requires phenol, toluene, o-cresol or m-cresol for TCE degradation. As characterized, Strain G4 (1) does not utilize the TOL pathway for toluene degradation; (2) does not appear to have the enzyme toluene dioxygenase, the first enzyme in the TOD pathway for toluene degradation, and (3) does not utilize the TMO pathway for toluene degradation. These three toluene degradative pathways (TOL, TOD. TMO) are summarized in U.S. patent application Ser. No. 177,631. Nelson et al. does not teach or disclose what genes, gene segments, enzymes, proteins or protein products are involved in Strain G4's ability to degrade TCE nor whether the genes involved are plasmid encoded or chromosomally encoded. Genetic engineering of the Strain G4 has not been reported.

More recently, Nelson et al., Appl. Environ. Microbiol., 54: 604-606 (1988) have tested the TCE-degradative ability of 6 microorganism strains capable of degrading naphthalene, biphenyl, phenol and toluene. Only 2 of the strains tested, *Pseudomonas putida* PpF1 (PpF1) and *Pseudomonas putida* B5 (B5), degraded TCE. PpF1 and B5 are toluene degrading strains, however a third toluene degrading strain *Pseudomonas putida* mt-2 (Pp mt-2) did not degrade TCE. Thus, it appears that not all toluene degrading strains are capable of degrading TCE.

Pp mt-2, which Nelson et al., supra, found could not degrade TCE, contains the pWWO plasmid, which plasmid codes for enzymes of the toluene degradation pathway known as TOL. PpF1, which Nelson et al., supra, found could degrade TCE, is known to contain enzymes of the toluene degradation pathway known as TOD. Wackett and Gibson, Appl. Environ. Microbiol., 54:1703-1708 (1988), have also recently shown that PpF1 cells have the ability to degrade TCE. Under their culture and assay conditions, Wackett and Gibson, supra, found that approximately 50% to 60% of input TCE (20 $\mu$M) was degraded. In contrast, at high TCE concentrations (320 $\mu$M) no TCE degradation could be detected. The highest TCE degradation rate that they observed was 1.8 nanomoles per minute per milligram of cell protein.

The genes for the TOD pathway of PpF1 are chromosomally encoded, in contrast to the plasmid encoded TOL pathway genes of Pp mt-2. Thus, it is not possible to predict whether genes involved in TCE degradation are chromosomally encoded or plasmid encoded. Studies by Nelson et al., supra, and Wackett and Gibson, supra, with mutants of PpF1 defective for various components in the TOD toluene degradative pathway suggest that the ability of PpF1 to degrade TCE is associated with toluene dioxygenase enzyme activity, which is the first enzyme in the chromosomally encoded TOD pathway. Studies by Nelson et al., supra, with Pp mt-2 showed that TCE degradative ability is not associated with any enzymes of the plasmid-encoded TOL pathway.

None of the microorganisms tested thus far for TCE degradative ability utilize the plasmid-encoded TMO pathway for toluene degradation. In addition, no microorganism has yet been genetically engineered to increase enzyme activity and TCE degradative ability. Furthermore, the use of any of the above described microorganism systems to degrade TCE has several associated problems. A first problem is that in order to degrade TCE, a degradative enzyme pathway (for example, the TOD pathway) must be induced in the microorganisms and the inducers that must be added to the TCE contaminated sample are hydrocarbons. A second problem is that since TCE (a substrate for the induced degradative enzymes) itself cannot be used by these microorganisms as a carbon source for cell growth, cells must be provided with another substrate (a cosubstrate) for growth. Such cosubstrates added to the TCE contaminated sample are hydrocarbons, such as toluene. These two problems are related to the practical problem that in order to degrade TCE in a contaminated sample such as an aquifer, it is not desirable to have to add hydrocarbons, such as toluene (as inducer and/or carbon source) because hydrocarbons like toluene are themselves environmentally toxic compounds. A third problem, closely related to the first two, is that in the above described systems where a hydrocarbon such as toluene acts as the inducer of and substrate for the degradative pathway enzymes (which enzymes both metabolize the hydrocarbon and degrade TCE), there is a competition between the hydrocarbon and TCE for the same enzyme system. Under conditions where the hydrocarbon concentration is in great excess over the TCE concentration, the hydrocarbon will compete more effectively for the enzyme system and delay TCE degradation. These three problems illustrate various aspects of what is termed the cosubstrate problem which occurs in the previously described inducible enzyme systems for TCE degradation.

SUMMARY OF THE INVENTION

It has now been unexpectedly found that PmKR1 and genetically engineered microorganisms containing PmKR1 toluene monooxygenase genes have the ability to degrade TCE. Consequently, PmKR1 and microorganism host cells containing PmKR1 toluene monooxygenase genes are useful in a method for degrading TCE.

The present invention thus encompasses a novel method for the degradation of TCE utilizing these microorganisms which contain PmKR1 toluene monooxygenase genes. In particular, the present invention encompasses a method for degrading TCE using genetically engineered microorganisms which have been developed and which have superior abilities to degrade a specific chemical contaminant such as TCE into innocuous materials.

Accordingly, one of the objects of the present invention is to provide a method for degrading TCE wherever it may appear as a contaminant or pollutant.

Another object of the present invention is to provide a method for the microbial degradation of TCE wherever desired, for example, as a means of cleaning up closed and open waters, industrial effluent discharges, government, commercial or industrial installations and plants or various laboratory operations, and in other situations where TCE may become accumulated. In particular, the present invention provides an improved method for degrading TCE using the genetically engineered TCE-degrading microorganisms of the present invention, when the TCE has been removed from contaminated waters (for example, by air-stripping).

A further object of the invention is to provide a procedure for degrading TCE readily, efficiently and relatively economically.

A still further object of the invention is to provide microorganisms containing recombinant plasmids with toluene monooxygenase genes from PmKR1 encoding enzymes that are capable of degrading TCE, leaving a non-toxic cell mass, these microorganisms being non-pathogenic to humans, animals or marine fauna and flora.

Yet another object of the invention is to provide a method for the degradation of TCE wherein the microorganism host cell containing the recombinant plasmid with the toluene monooxygenase genes from PmKR1 and capable of degrading TCE can be applied directly to the locus of TCE contamination.

A further object of the invention is to provide a method of degrading TCE using genetically engineered microorganisms with PmKR1 toluene monooxygenase genes in which the genes are placed under the control of various promoters, and result in enhanced expression of toluene monooxygenase activity and enhanced degradation of TCE. under certain cell culture and assay conditions.

Another object of the invention is to provide a method of degrading TCE using genetically engineered microorganisms with PmKR1 toluene monooxygenase genes in which the genes are placed under the control of promoter systems which are not induced by hydrocarbons, such as toluene, thereby solving the cosubstrate problem presented by previously described inducible enzyme systems for TCE degradation. Advantages of the use of genetically engineered microorganisms in the present invention thus include: the elimination of a hydrocarbon such as toluene as inducer; the elimination of a hydrocarbon such as toluene as cosubstrate for the degradative enzyme system; and the elimination of competitive inhibition of TCE degradation by the hydrocarbon cosubstrate/inducer.

The invention provides a method for the microbial degradation of TCE comprising treating TCE with PmKR1 cells or PpY2101 cells containing the pAUT1 plasmid from PmKR1 or a microorganism host cell containing a recombinant plasmid. The recombinant plasmid contains toluene monooxygenase genes isolated from PmKR1. The genes encode enzymes and proteins of the TMO pathway for toluene degradation. According to the method, PmKR1 cells or PpY2101 cells or microorganism host cells with a recombinant plasmid are treated with an inducer of the toluene monooxygenase genes.

An advantage of the present invention in one of its aspects is that use is made of genetically engineered microorganisms, with well-characterized cloned genes whose expression is under the control of very well characterized and easily regulated promoters, such that these genetically engineered microorganisms have the capability of efficiently degrading TCE. In addition, these genetically engineered microorganisms can be rapidly and inexpensively grown to very high cell densities with the modern fermentation technology that has been developed for strains of E. coli, in contrast to the difficulty of growing natural isolates such as the PmKR1 cells. Furthermore, these genetically engineered microorganisms can sustain, in the presence of low concentrations of glucose, TCE degradation for periods in excess of 12 hours. A further advantage of using these recombinant microorganisms is that they are able to degrade TCE to extremely low levels by virtue of the fact that metabolism no longer requires the presence of aromatic hydrocarbons (such as toluene) in the medium, such as is required by the PmKR1 cells.

The genetically engineered microorganisms may be applied directly to the TCE containing environment to be decontaminated. Alternatively, enzyme products of the cloned genes may be used to degrade TCE. rather than the genetically engineered microorganisms, in loci of TCE chemical waste. Acceleration of the rate of decontamination results from the use of such genetically engineered microorganisms with inducible genes for the degradation of TCE.

These and other objects and advantages of the present invention will become apparent to those skilled in the art from a consideration of the following detailed description and claims.

BRIEF DESCRIPTION OF THE DRAWINGS

Referring to the accompanying drawings, there are provided 8 figures, to be hereinafter described in detail, illustrating this invention in which.

DETAILED DESCRIPTION OF THE PREFERRED EMBODIMENTS

As stated above, TCE is a major industrial solvent and has been found to be widely distributed in the aquatic environment. Approximately 234,000 metric tons of TCE are produced annually worldwide (U.S. Environmental Protection Agency, 1980, EPA 440/5-80-077). TCE is very persistent and can be extremely difficult to remove once present in the environment. At present, little is known about the microbial metabolism of TCE. Isolated and cloned genes, such as the PmKR1 toluene monooxygenase genes used in the present invention, should permit the elucidation of a detailed understanding of a unique type of microbial TCE metabolism. In addition, the cloned genes may be manipulated, for example, by combining the genes with different promoters, to increase expression of the enzyme products so as to increase the rate and extent of degradation of TCE. As illustrated in the present invention, the use of certain promoter systems under certain cell culture and assay conditions may increase expression of toluene monooxygenase gene products and may result in the acceleration of the rate of TCE degradation by microorganisms containing these cloned genes.

Development of genetically engineered microorganisms which have superior abilities to degrade specific chemical contaminants such as TCE to innocuous materials is one important strategy in the development of cost effective and environmentally sound methods for hazardous chemical waste cleanup. The development and use of microorganism host cells with recombinant plasmids containing toluene monooxygenase genes from PmKR1 in the present invention is a new and useful method that may be applied to TCE chemical waste cleanup. In particular, these genetically engineered microorganism host cells are useful in an improved method for degrading TCE when the TCE has been removed from contaminated waters (for example, by air-stripping). These genetically engineered microorganism host cells with PmKR1 toluene monooxygenase genes have been fully described in U.S. patent application Ser. No. 177,631 which has been incorporated by reference in its entirety.

It is also contemplated that the enzyme products of the toluene monooxygenase genes may be used to degrade TCE, rather than using the microorganism host cells containing recombinant plasmids with toluene monooxygenase genes to degrade the TCE. The enzyme products may be applied directly to loci of TCE chemical waste.

The present invention provides a method that may be used to degrade TCE in whatever locations it may appear as a contaminant or pollutant. Thus, with the method, it becomes possible to clean up and degrade TCE in loci of TCE chemical waste found in water or soil.

The following examples are given merely as illustrative of the present invention and are not to be considered as limiting.

EXAMPLE 1

Bacterial Strains and Growth

The bacterial strains listed below are described in U.S. patent application, Ser. No. 177,631 which has been incorporated by reference. In particular, the construction and characteristics of the genetically engineered microorganism host cells including plasmids, vectors, genes and gene segments are described in the above referenced application. The following bacterial strains were grown overnight at 30° C. in PAS medium (Chakrabarty et al., *Proc. Natl. Acad. Sci. U.S.A.* 70: 1137–1140, 1973) supplemented with the following growth substrates and inducers: PmKR1, toluene (supplied as vapor) for growth and induction of toluene degradative enzymes or 0.2% glucose for growth; *Pseudomonas putida* F1 (PpF1), toluene (supplied as vapor) for growth and induction of toluene degradative enzymes or 0.2% glucose for growth; *Pseudomonas putida* KT2440 (KT2440), 0.2% L-glutamate for growth, *Pseudomonas putida* KT2440 containing plasmid pND50 (KT2440/pND50). 2.5 mM p-cresol (diluted 1,000 fold from a concentrated stock in dimethyl formamide) for growth and induction of p-cresol degradative enzymes; *Pseudomonas putida* KT2440 containing plasmid pAUT1 (KT2440/pAUT1), toluene (supplied as vapor) for growth and induction of toluene degradative enzymes; *Pseudomonas mendocina* Y4001 (PmY4001), 2.5 mM p-cresol for growth and induction of p-cresol degradative enzymes; E. coli strain HB101 containing recombinant plasmids pKY277, pMY402, or plasmid vector pMMB66EH (HB101/pKY277, HB101/pMY402, HB101/pMMB66EH respectively), 0.2% L-glutamate or 0.2% glucose, 0.2% casamino acids and 2 $\mu$g/ml vitamin B1 for growth, 250 $\mu$g/ml ampicillin for plasmid maintenance, and 1 mM isopropyl $\beta$-D-thiogalactoside (IPTG) for induction of toluene monooxygenase synthesis; KT2440 containing recombinant plasmid pMY402 (KT2440/pMY402), 0.2% L-glutamate for growth, 1 mg/ml ampicillin for plasmid maintenance, and 5 mM IPTG for induction of toluene monooxygenase synthesis; *E. coli* FM5 containing recombinant plasmid pKY287 or plasmid vector pCFM1146 (FM5/pKY287 and FM5/pCFM1146, respectively), 0.2% glucose and 0.05% yeast extract for growth, 50 $\mu$g/ml kanamycin for plasmid maintenance, and for FM5/pKY287 a temperature shift of culture to 42° C. for 2 hours and then return to 30° C. for 2 hours for induction of toluene monooxygenase synthesis. Cells were grown to at least an OD$_{550}$ equal to 0.5, which corresponds to about $3 \times 10^8$ CFU/ml.

In addition to the above listed strains, several newly isolated strains designated E1, E2, E4, E5, E7 and E9 which utilize ethylbenzene or toluene as a carbon source for growth were grown and tested for TCE degradative ability. The ethylbenzene utilizing strains were isolated as follows. Seven samples (numbered 1–7) were obtained from the LaBrea Tarpit and nine samples (numbered 1–9) from the Thousand Oaks Sewage Treatment Plant. An aliquot of 1 ml from each sample was inoculated into 50 ml of PAS medium supplemented with ethylbenzene supplied as vapor from 0.2 ml ethylbenzene and the cultures were grown at 25° C. for 5 days. Cultures numbered 1, 4, 5, and 9 from Thousand Oaks Sewage Treatment Plant and cultures numbered 2 and 7 from LaBrea Tarpit were grown to saturation (no growth was obtained from other cultures). An aliquot of 1 ml was taken from cultures 1, 2, 4, 5, 7 and 9 and each was inoculated with 50 ml PAS medium supplemented with ethylbenzene supplied as vapor as described above. These 50 ml cultures were allowed to grow overnight at 25° C. A sample from each culture was streaked on a PAS-ethylbenzene plate twice for single colonies. The purified colonies from each sample were designated E1, E2, E4, E5, E7 and E9. These natural bacterial isolates which utilize ethylbenzene were also found to grow on toluene and were grown overnight at 30° C. in PAS medium supplemented with the following growth substrates and inducers: 0.2% L-glutamate for growth, 1 mM toluene for induction of toluene degradative enzymes. Cells were grown, as described for other strains listed above, to at least $OD_{550}$ equal to 0.5.

EXAMPLE 2

Radioactivity Assay for TCE Degradation

This example discloses a radioactivity assay measuring the appearance of non-volatile metabolites of TCE. Bacterial strains used in this assay were grown as in Example 1. If necessary, the cells were diluted with PAS medium to an $OD_{550}$ of 0.5 for the assay. To 4 ml of cell suspension in a 50 ml serum vial was added TCE (1,2-$^{14}$C, 72 mCi per mmole, New England Nuclear, Boston, Mass.) to 5 μM final concentration. The solution of $^{14}$C-TCE was prepared by mixing radioactive and non-radioactive TCE to give a 5 mM solution in dimethyl formamide at about $1 \times 10^6$ counts per minute per μl. Four μl of solution was added to each 4 ml cell suspension, the serum vial was stoppered with a teflon coated rubber septum and a metal crimp cap, vortexed, and incubated with shaking at 30° C. At zero time and at 30 minute intervals thereafter, about 100 μl of the cell suspension was withdrawn using a needle and syringe and 20 μl of this was spotted onto a small section of a Whatman silica gel thin layer chromatography plate (Whatman. Clifton, N.J.), air dried for 15 minutes, and counted in a Beckman LS-100 scintillation counter (Beckman Instruments, Inc., Palo Alto. Calif.) using Biofluor (New England Nuclear) liquid scintillation fluid. For Table 1, data obtained after air drying were converted to nanomoles of TCE metabolized to non volatile material by using 200 counts per minute per picomole as the specific activity of the input $^{14}$C-TCE.

TABLE 1

TCE Degradation

| Strain | Inducer | Nanomoles of $^{14}$C-TCE Converted to Non-Volatile Material in 2 hours |
|---|---|---|
| PpF1 | none | 0.4 |
|  | toluene | 1.1–2.0 |
| PmKR1 | none | 0.4 |
|  | toluene | 5.1–6.5 |
| PmY4001 | p-cresol | 0.4 |
| PpY2101 | none | 0.4 |
|  | toluene | 3.8–5.1 |
| PpY2119 | p-cresol | 0.4 |
| PpY2118 | none | 0.4 |
|  | IPTG | 0.7–1.1 |
| HB101/pKY277 | none | 0.4 |
|  | IPTG | 1.6 |
| HB101/pMY402 | none | 0.3, 0.5 after 6 hrs. |
|  | IPTG | 3.3–3.5, 4.7 after 6 hrs. |

Table 1 summarizes the extend of $^{14}$C-TCE conversion to non-volatile material in 2 hours as a function of inducer present during overnight growth. In these experiments, about 0.4 nanomoles of $^{14}$C-TCE were not volatilized; this represents a background of about 2% of the input $^{14}$C-TCE.

EXAMPLE 3

Gas Chromatography Assay for TCE Degradation

This example discloses a gas chromatography assay measuring the disappearance of volatile TCE. Bacterial strains used in this assay were grown as described in Example 1. Overnight cultures were diluted (if necessary) to an $OD_{550}$ of 0.5 in PAS medium for the assay and 4 ml of cell culture was added to serum vials. TCE (Aldrich, (Milwaukee, Wis.). spectrophotometric grade) was diluted in N,N'dimethylformamide (DMF) (Aldrich, spectrophotometric grade) to 10 mM or 20 mM and 4 μl added to cell suspension to give a final TCE concentration of 10 μM (1.3 ppm) (FIG. 1) or 20 μM (2.6 ppm) (FIG. 2). Vials were stoppered, vortexed, and 10 μl of gas phase were withdrawn using a gas-tight syringe at the times indicated in the figures. Gas phase samples were analyzed on a Hewlett-Packard 5890A gas chromatograph equipped with a 25 meter 5% phenyl methyl silicone column (Hewlett-Packard, Palo Alto, Calif.) and a $^{63}$Ni electron capture detector. The injector, oven, and detector temperatures were 120°, 100°, and 300°, respectively. The carrier gas was helium and the makeup gas was 95% argon-5% methane. Peak areas were calculated by a Hewlett-Packard 3392A Integrator. Data are presented in FIGS. 1, 2, and 3 as the percentage of TCE remaining at various times after addition to the cell suspension. The amount of TCE present at zero time is taken to be 100%.

Figure 1:
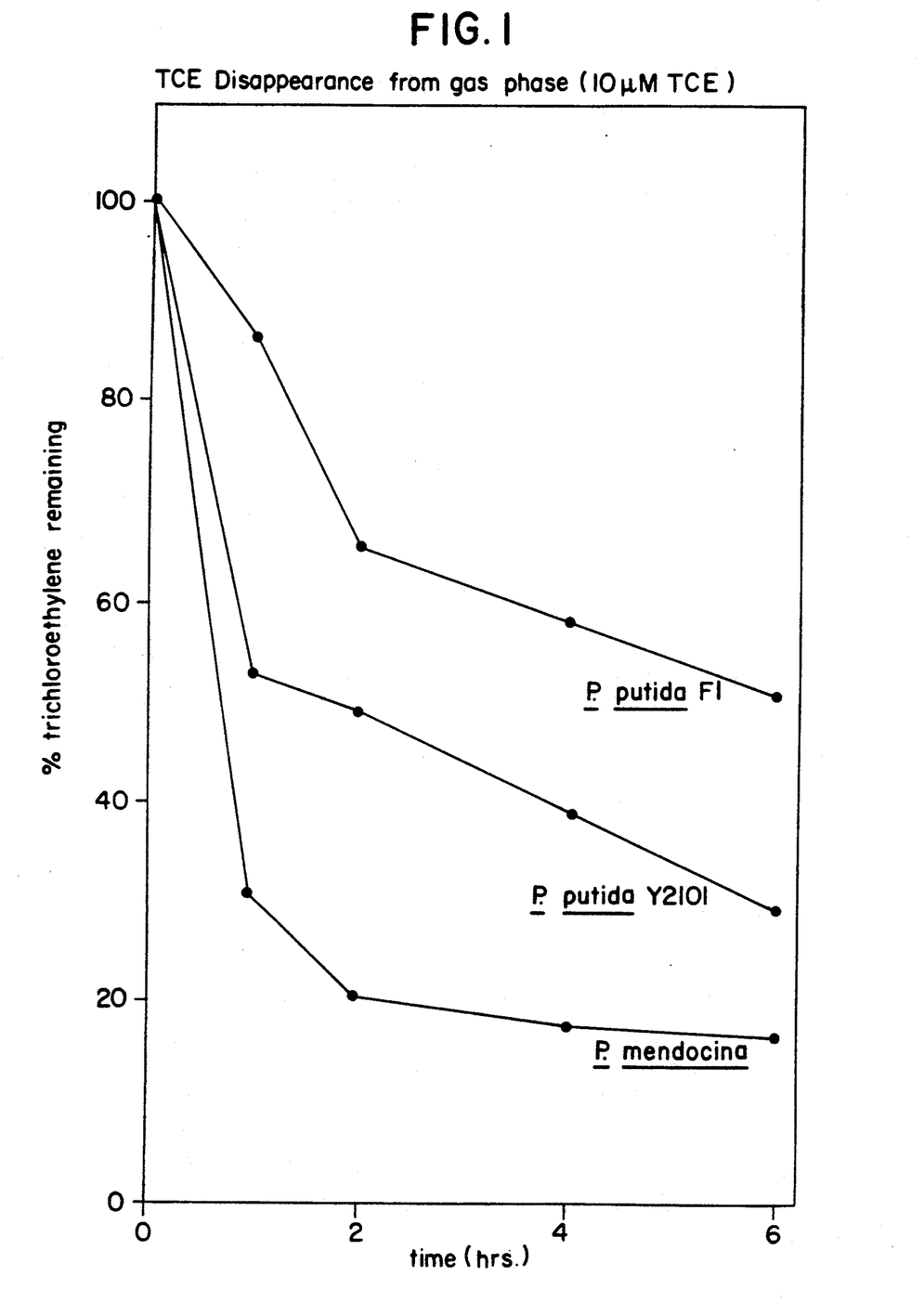
FIG. 1 is a graph showing the disappearance of 10 $\mu$M (1.3 ppm) TCE added to cells tested for TCE degradative ability due to the metabolism of TCE by the cells into non-volatile material as a function of time. Cells tested were Pseudomonas mendocina KR-1 (PmKR1), Pseudomonas putida F1 (PpF1) and Pseudomonas putida Y2101 (Pp Y2101).
Figure 2:
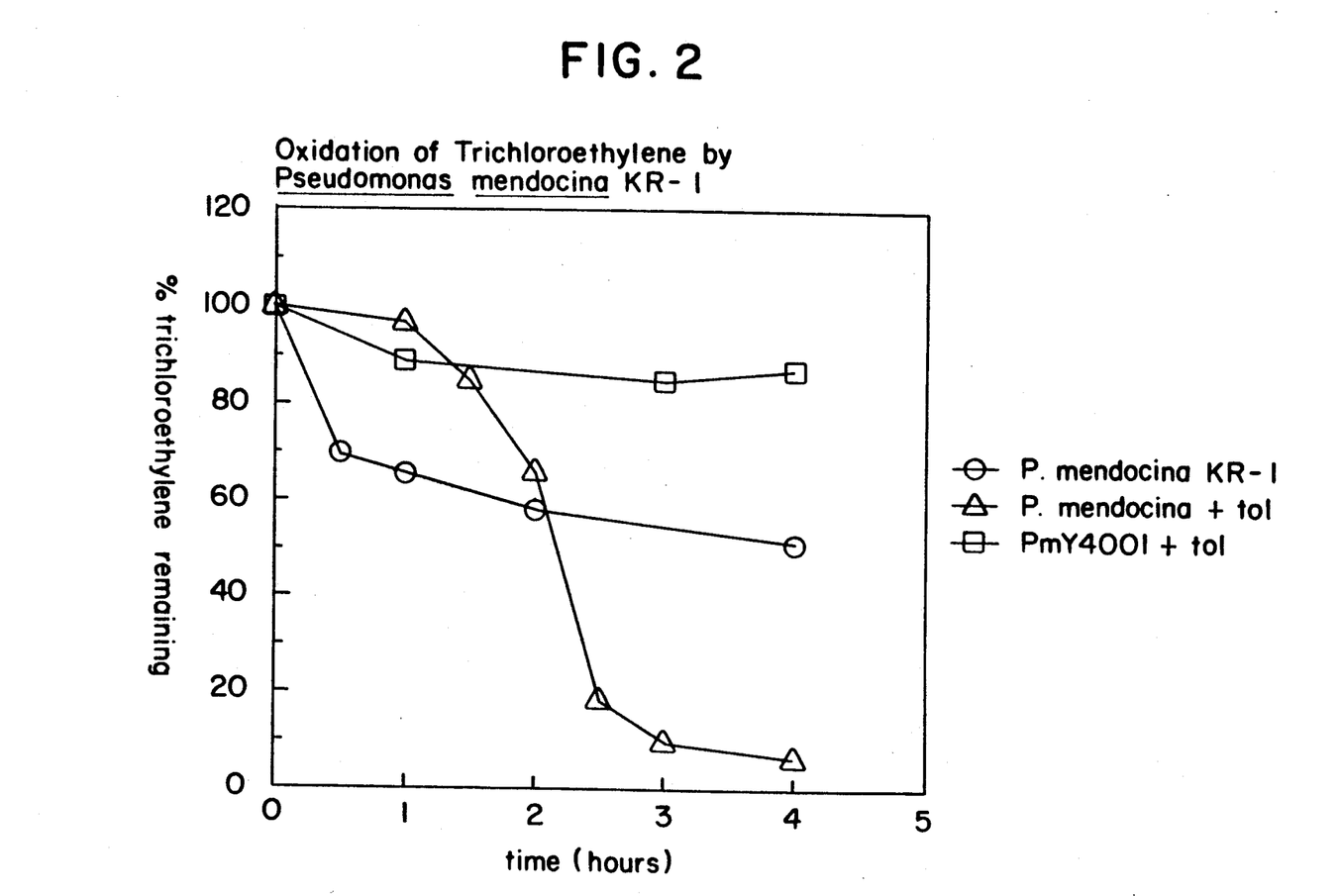
FIG. 2 is a graph showing the effect of adding toluene at the time of TCE addition on the disappearance of 20 $\mu$M (2 6 ppm) TCE added to cells tested for TCE degradative ability due to the metabolism of TCE into non-volatile material as a function of time. Cells tested were: (1) PmKR1 with and without toluene added at the time of TCE addition, and (2) PmY4001.

FIG. 1 shows the rate of TCE degradation at 10 μM (1.3 ppm) TCE for PmKR1. KT2440/pAUT1, and PpF1. Degradation is rapid at 1-2 hours after TCE addition, and slows down at later times, PmKR1 shows the highest activity of the three strains tested.

FIG. 2 shows stimulation of TCE degradation by PmKR1 cells pre-grown in PAS medium containing toluene, when toluene is present at the time of TCE addition. PmKR1 will degrade greater than 90% of TCE initially present at 20 μM (2.6 ppm) when toluene is present as vapor; only approximately 50% of TCE is degraded by PmKR1 when toluene is not present at the time of TCE addition.

Figure 3:
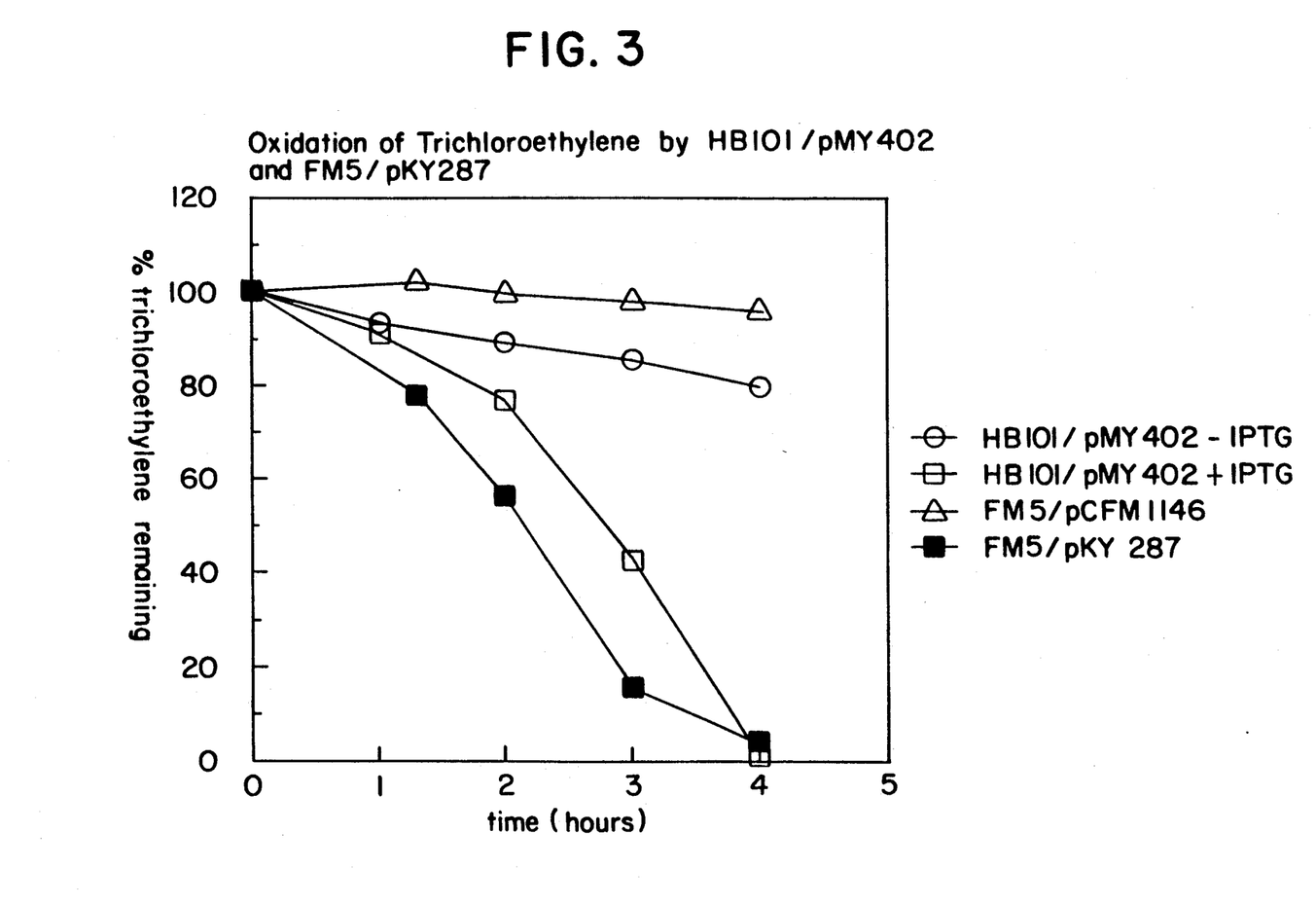
FIG. 3 is a graph showing the disappearance of 50 $\mu$M (6.5 ppm) TCE added to cells tested for TCE degradative ability due to the metabolism of TCE into non-volatile material as a function of time. Cells tested were: (1) E. coli HB101 containing recombinant plasmid pMY402 (HB101/pMY402) under conditions where the cells had been induced with IPTG prior to and during the assay (control cells were not induced with IPTG); and (2) E. coli FM5 cells containing recombinant plasmid pKY287 (FM5/pKY287) where the cells had been induced with an increase in temperature (control cells were FM5 cells containing the plasmid vector pCFM1146).

FIG. 3 shows the rate of TCE degradation at 20 μM (2.6 ppm) by HB101/pMY402 cells and FM5/pKY287 cells. Greater than 95% of the TCE is degraded after 4 hours.

EXAMPLE 4

TCE Degradation by Natural Bacterial Isolates

The ethylbenzene (and toluene) utilizing strains isolated and grown as described in Example 1 were assayed for their ability to degrade TCE. TCE levels were assayed by gas chromatography according to Example 3. TCE was added to 20 μM (2.6 ppm). The results are shown in Table 2. When compared with wildtype PmKR1 cells, the percent TCE remaining after an 18 hour degradation period was 6–14 times greater than that for wildtype PmKR1 cells, indicating that these strains were substantially less effective than wildtype PmKR1 cells in their ability to degrade TCE.

TABLE 2

TCE Degradation by Natural Bacterial Isolates

| Strain | % TCE remaining after 18 hours |
|---|---|
| PmKR1 | 4 |
| PmY4001 | 84 |
| PpF1 | 49 |
| E1 | 48 |
| E2 | 39 |
| E4 | 56 |
| E5 | Not Tested |
| E7 | 38 |
| E9 | 24 |

TCE levels assayed by gas chromatography according to Example 3. TCE added to 20 $\mu$M (2.6 ppm). In this experiment, the E1, E2, E4, E5, E7 and E9 cells were grown on toluene as carbon source, although as described in Example 1, these cells were originally selected for growth on ethylbenzene.

EXAMPLE 5

Effect of Higher TCE Concentrations

Figure 4:
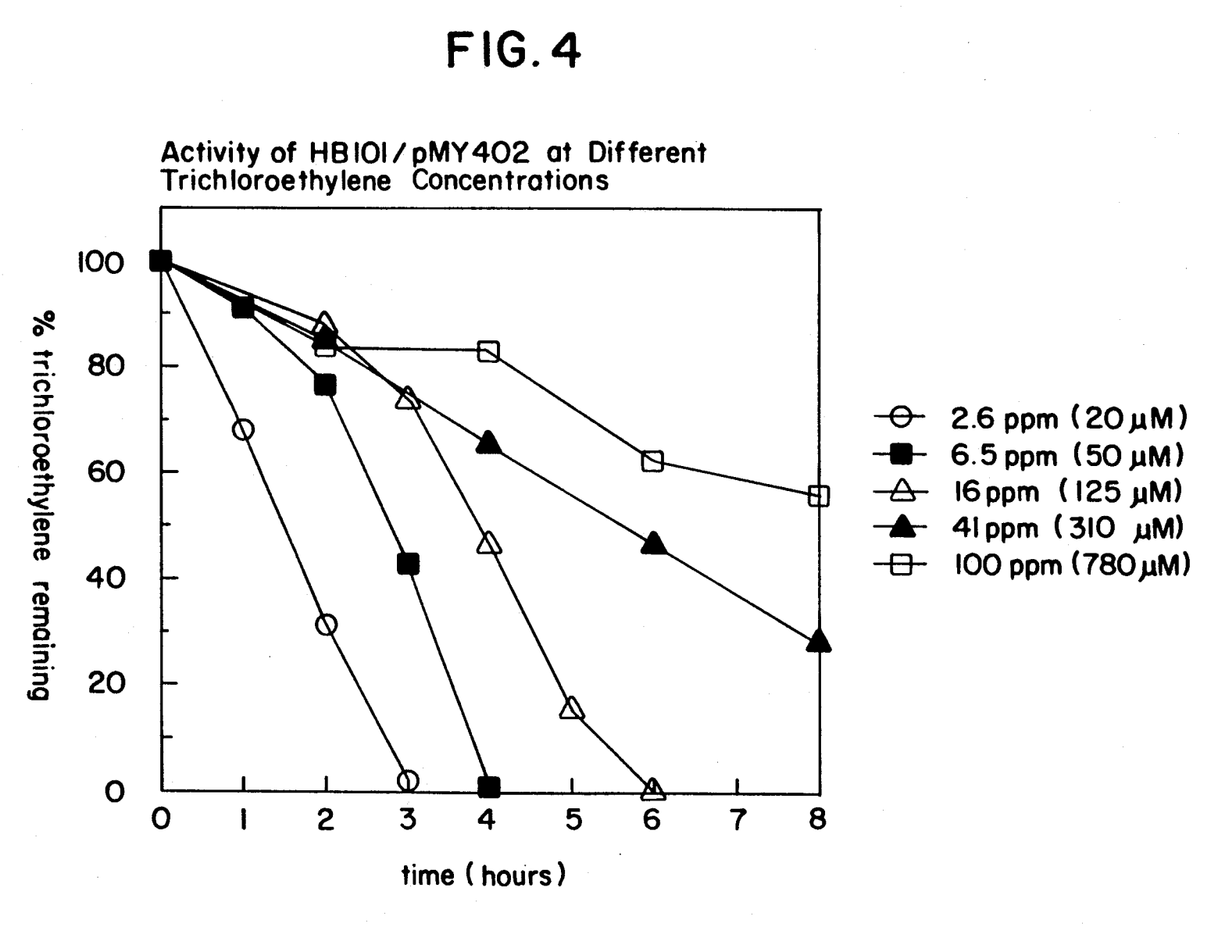
FIG. 4 is a graph showing the disappearance of TCE added to the cells in varying concentrations due to metabolism of TCE into non-volatile material as a function of time, by HB101 cells containing the pMY402 recombinant plasmid.

This example discloses the degradation of increasing TCE concentrations by recombinant cells of the present invention. Bacterial cells in this assay were grown as in Example 1, except that 0.5% yeast extract (Difco, Detroit, Mich.) was substituted for casamino acids and vitamin B1 in growth medium. The assay was the gas chromatography assay for TCE degradation described in Example 3. FIG. 4 shows the disappearance of TCE added to the cells in varying concentrations from the gas phase due to the metabolism of TCE into nonvolatile material as a function of time by HB101 cells containing the pMY402 recombinant plasmid (pMMB66EH plasmid vector with PmKR1 toluene monooxygenase genes). The open circles show the metabolism of 20 $\mu$M (2.6 ppm) TCE; the open squares show the metabolism of 50 $\mu$M (6.5 ppm) TCE; the open triangles show the metabolism of 125 $\mu$M (18 ppm) TCE; the closed squares show the metabolism of 312 $\mu$M (48 ppm) TCE; and the closed triangles show the metabolism of 780 $\mu$M (120 ppm) TCE. Controls were performed for each TCE concentration using HB101 cells containing pMY402 plasmid in the absence of the inducer IPTG or HB101 cells containing the pMMB66EH plasmid vector.

FIG. 4 shows that HB101 containing pMY402 induced with IPTG metabolizes nearly 100% of TCE at concentrations of TCE up to nearly 20 ppm in 6 hours or less. At 48 ppm TCE, 75% is metabolized in 8 hours. In addition, FIG. 4 shows that increased rates of TCE degradation occur at increased concentrations of TCE.

EXAMPLE 6

Kinetics of TCE Degradation

In order to study the kinetics of TCE degradation by the PmKR1 toluene monooxygenase gene products, PmKR1 and PmY4001 cells were grown as in Example 1. In addition, for these experiments, FM5/pKY287 and FM5/pCFM1146 cells were grown as follows: an inoculum of cells was added to L-broth and the culture was incubated at 30° C. until the cells reached an OD$_{550}$ of 0.5, then the temperature was shifted to 42° C. for 1.5 hours to permit enzyme induction and synthesis, then returned to 30° C. for 4-6 hours for continued growth. The cell cultures were centrifuged and resuspended in PAS medium or PAS medium containing 0.2% glucose.

In order to determine the kinetics of TCE degradation, the cell cultures were diluted with 0.1 M KPO$_4$, pH 7.5, to an OD$_{550}$ as indicated in Table 3 below. A portion of the diluted cells was saved for protein assays as described below. TCE degradation was assayed by gas chromatography in substantial accordance with the procedure described in Example 3, except that 10 ml (instead of 4 ml) cell reactions were done in serum vials, and 5-10 $\mu$l of TCE in DMF were added to the cells at the final concentrations indicated in Table 3 below. The cell reactions were incubated with shaking at 30° C. and at 0 time and at various times after TCE addition, 10 $\mu$l of gas phase were withdrawn and analyzed for TCE concentration as described in Example 3. Initial rates of TCE degradation were calculated from the amount of TCE degraded during the initial 20 to 30 minutes of the reaction and are reported as nanomoles per minute per mg protein in Table 3 below. Most kinetic experiments were performed using FM5/pKY287 cells, however, several experiments were performed using PmKR1 cells, in order to compare the rates using recombinant cells with the rates using wild-type cells. FM5/pCFM1146 cells were used as control cells for FM5/pKY287 cells, and PmY4001 cells were used as control cells for PmKR1 cells, in order to measure any loss of TCE due to leakage from the vial or due to adsorption to cells. The experiments showed that loss from control vials was usually less than 5% after a 1 hour incubation at 30° C.

Total cell protein may be assayed by a variety of procedures including the method of Bradford, Anal. Biochem. 72:248-254 (1976), commercially available as the Bio-Rad Protein Assay (Bio-Rad, Richmond, Calif., catalog no. 500-0006). To lyse cells and expose cellular protein for reaction in the protein assay procedure, sodium hydroxide was added to cell suspensions to 0.1 N final concentration, followed by incubation at 100° C. for 30 minutes prior to the assay procedure. Bovine plasma albumin, treated with NaOH and heat as just described, was used as a protein standard in the assay procedure. The rates of TCE degradation by FM5/pKY287 cells at varying cell densities (OD$_{550}$ of 0.05 to 1.00) and varying TCE concentrations (1 to 40 $\mu$M; 0.13 to 5.2 ppm) are reported in Table 3.

TABLE 3

Kinetics of TCE Degradation by FM5/pKY287 Cells (nmoles/min/mg protein)

| Initial Cell Density (OD$_{550}$) | TCE Concentration ($\mu$M) | | | | | |
|---|---|---|---|---|---|---|
| | 1 | 2.5 | 5.0 | 10.0 | 20.0 | 40.0 |
| 0.05 | — | — | — | — | 1.2 | — |
| 0.10 | 0.4 | 0.5 | 1.5 | 1.3 | 1.0 | 0.1 |
| 0.20 | — | — | — | — | 1.4 | — |
| 0.50 | — | — | 0.9 | — | 1.4 | — |
| 1.00 | — | — | — | — | 0.2 | — |

In experiments with PmKR1 cells that had been induced with toluene, the rates of TCE degradation at an OD$_{550}$ of 0.50 and at a TCE concentration of 5.0 $\mu$M and 20.0 $\mu$M were 1.3 and 2.4 nmoles/min/mg protein, respectively. At an OD$_{550}$ of 1.0 and a TCE concentration of 5 $\mu$M, the rate of TCE degradation by PmKR1 cells was 2.7 nmoles/min/mg protein. These results indicated that the rate of TCE degradation of the wild-type PmKR1 cells is at least comparable to, and is generally slightly higher than, the rate of the recombinant cells. The results in Table 3 also demonstrate that the recombinant FM5/pKY287 cells can effectively degrade TCE at low cell density (OD$_{550}$ of 0.05-0.10) and at low TCE concentrations (1 $\mu$M-2.5 $\mu$M). Thus, even at low cell densities, these cells may be used in an efficient process for TCE degradation.

EXAMPLE 7

Metabolism of $^{14}C$-TCE

In order to trace the metabolism of $^{14}C$-TCE by the PmKR1 toluene monooxygenase gene products, PmKR1 cells, PmY4001 cells and HB101 cells containing pMY402, were grown as in Example 1 and incubated as described in paragraph 1 of Example 2. Incubation was for 16–18 hours at 30° C. Conversion of $^{14}C$-TCE to $^{14}CO_2$, $^{14}C$ in cell mass and $^{14}C$ in growth medium was measured as described in Nelson et al., *Appl. Environ. Micro.* 53: 949–954 (1987) and Spain Nishino, *Appl. Environ. Micro.* 53: 1010–1019 (1987).

Briefly, after the incubation period, the medium was acidified with 100 μl of 2 N sulfuric acid. $^{14}CO_2$ was purged from the aqueous phase by running an airline into the vial and bubbling air for a period of 1–2 hours, while releasing and directing the air containing $^{14}CO_2$ through another line into a tube containing 5 ml. of 1 N sodium hydroxide. The radioactivity in 0.5 ml of the sodium hydroxide solution was determined and the percentage of $^{14}C$ as $CO_2$ in the 5 ml sample was calculated. After removal of $^{14}CO_2$ as just described, a 1 ml aliquot of the cell suspension was removed and the radioactivity of the cell suspension was determined. The remaining suspension of medium and cells was removed from the vial, centrifuged to pellet the cells and the supernatant was passed through a 0.2μ filter. The radioactivity of a 50 μl aliquot of the filtrate was determined and the percentage of $^{14}C$ in the medium was calculated. The difference between the radioactivity in the cell suspension and the filtrate was taken to be the radioactivity present in the cell mass. Alternatively, the $^{14}C$ in the cell mass could be counted directly by resuspending the cell pellet and counting an aliquot of the resuspended cells. The results of a representative experiment using PmKR1, PmY4001, and HB101/pMY402 cells are summarized in Table 4.

TABLE 4

| | $^{14}C$-TCE Metabolism | | |
|---|---|---|---|
| Strain | % $^{14}C$ as $CO_2$ | % $^{14}C$ in Cell Mass | % $^{14}C$ in Medium |
| P. mendocina KR-1 | 34 | 12 | 32 |
| P. mendocina Y4001 | 1 | 5 | 9 |
| HB101/pMY402 (+IPTG) | 18 | 14 | 39 |
| HB101/pMY402 (−IPTG) | 4 | 4 | 13 |

In other experiments. PmKR1, PmY4001, FM5/pKY287 and FM5/pCFM1146 cells were grown as in Example 1, and then incubated with $^{14}C$-TCE. The reaction with $^{14}C$-TCE was carried out as described above except that: (i) $^{14}CO_2$ was purged from the aqueous phase and trapped in 20 ml of 1 N sodium hydroxide; and (ii) 1.2 ml of 1 M $BaCl_2$ were added to 5 ml of the 20 ml sodium hydroxide solution to precipitate the $^{14}CO_2$. The resulting precipitate was analyzed for $^{14}C$ along with an aliquot of the supernatent. The results are summarized in Table 5. Nearly all of the $^{14}C$ present in the 1 N sodium hydroxide solution was precipitated by $BaCl_2$, confirming that the $^{14}C$ present was $^{14}CO_2$.

TABLE 5

| | Table $^{14}C$-TCE Metabolism | | |
|---|---|---|---|
| Strain | % $^{14}C$ as $CO_2$ | % $^{14}C$ in Cell Mass | % $^{14}C$ in Medium |
| P. mendocina KR-1 | 32 | 31 | 31 |
| P. mendocina Y4001 | <1 | 1 | 2 |
| FM5/pKY287 | 45 | 18 | 39 |
| FM5/pCFM1146 | <1 | 1 | 2 |

Figure 5:
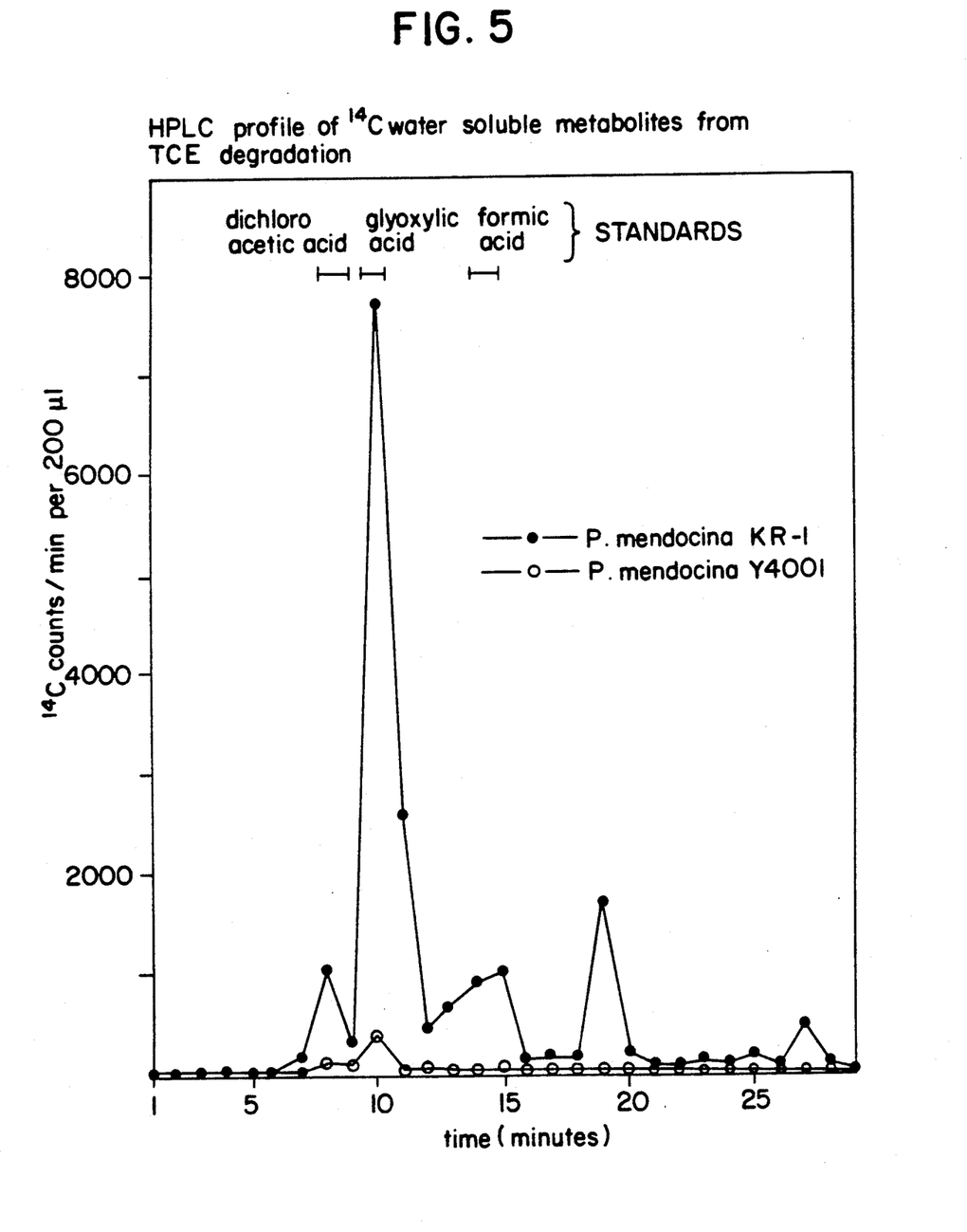
FIG. 5 is a graph showing an HPLC elution profile of $^{14}$C metabolites present in the cell medium after the degradation of $^{14}$C-TCE by PmKR1 cells (control cells were PmY4001 cells).
Figure 6:
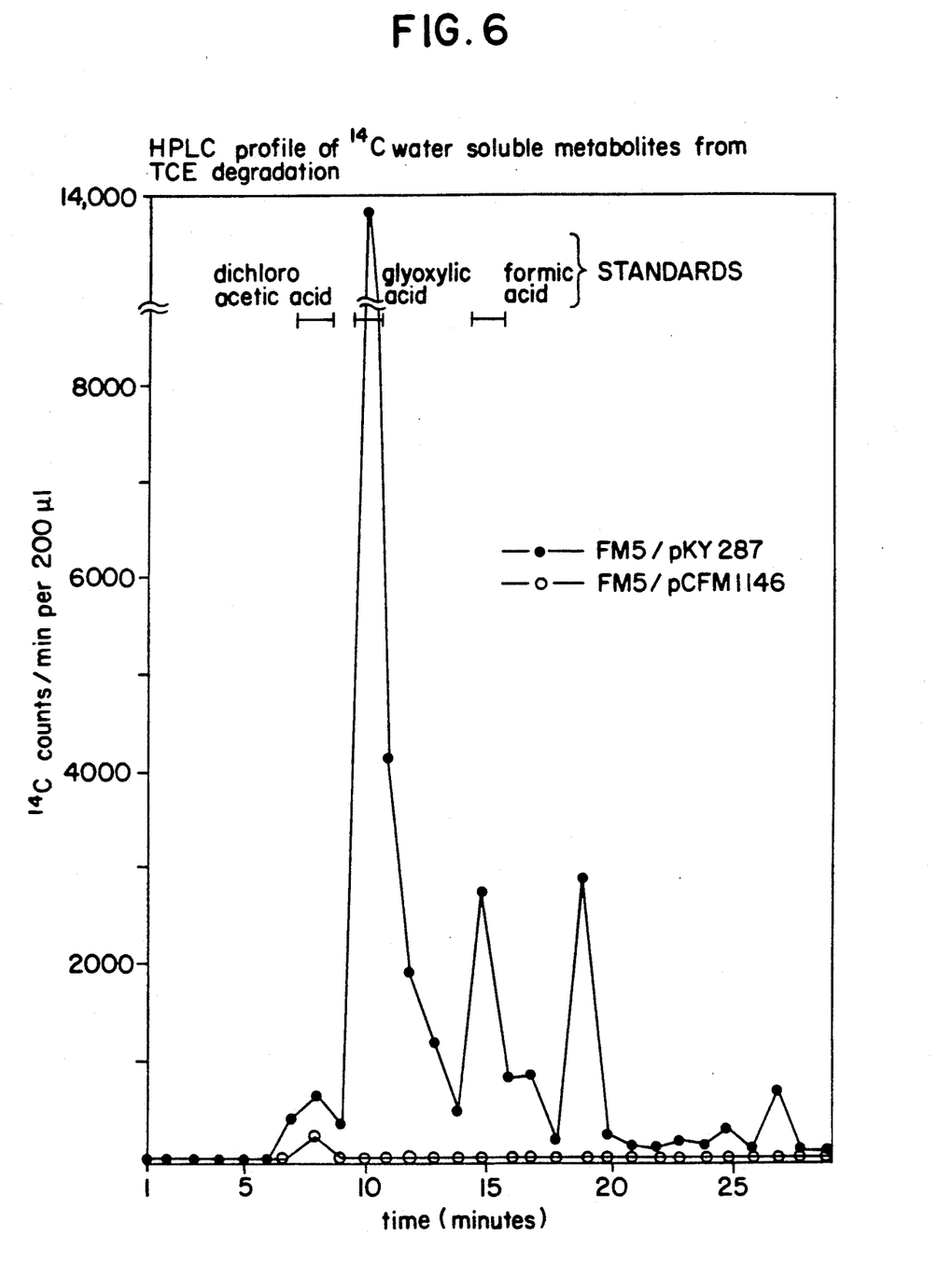
FIG. 6 is a graph similar to FIG. 5 but in which the degradation of $^{14}$C-TCE was by FM5/pKY287 cells (control cells were FM5/pCFM 1146 cells).

In order to further analyze what metabolites were present in the cell medium, each cell medium fraction in Table 5 was treated as follows. Three drops of 45% KOH were added to the 10 ml of cell medium containing $^{14}C$ labeled water soluble metabolites in order to bring the pH of the solution to 11–12. The solution was lyophilized for 16–18 hours to a final volume of 0.4–0.6 ml with a 60–70% recovery of $^{14}C$ labeled material. The concentrated material was analyzed by high pressure liquid chromatography (HPLC), using an Aminex ion exclusion column (Bio-Rad) and 0.01 N $H_2SO_4$ as eluant. Fractions of 0.6 ml were collected and the $^{14}C$ in 0.2 ml of each fraction was determined as shown in FIGS. 5 and 6. Identification of the $^{14}C$ labeled products was determined by comparing HPLC elution times with the elution times of unlabeled standards, as shown in FIGS. 5 and 6. The standards used were: monochloroacetic acid, dichloroacetic acid, glyoxylic acid and formic acid.

A summary of the $^{14}C$ metabolic products from TCE degradation by PmKR1 cells (FIG. 5) and FM5/pKY287 cells (FIG. 6) is presented in Table 6.

TABLE 6

| | Analysis of Cell Medium for TCE Degradation Products | |
|---|---|---|
| | % $^{14}C$ in Cell Medium | |
| Compound | PmKR1 | FM5/pKY287 |
| Dichloroacetic acid | 9 | 5 |
| Glyoxylic acid | 64 | 71 |
| Formic acid | 16 | 15 |
| Unidentified compound | 11 | 10 |

Of the total $^{14}C$-TCE added to the PmKR1 or FM5/pKY287 cells (note that approximately 30–40% of the total $^{14}C$ was found in the cell medium fraction), about 3–5% of the total $^{14}C$ was identified as a chlorinated compound, dichloroacetic acid. The remainder of the $^{14}C$ radioactivity was recovered as $CO_2$ (~30–45%), innocuous cell constituents in the cell mass (~18–35%) or predominantly nonchlorinated water soluble components found in the cell medium (~25–35%).

EXAMPLE 8

Dechlorination of TCE

This example discloses an assay that measures the release of chloride ions from TCE by PmKR1 cells or microorganism host cells containing a recombinant plasmid with PmKR1 toluene monooxygenase genes.

PmKR1 and FM5/pKY287 cells were grown as described in Example 1. After cell growth, bacterial cultures were centrifuged at 5,000 rmp for 5 minutes, growth medium was discarded and pelleted cells were resuspended in 15 ml. of 0.1 M potassium phosphate, pH 7.0, centrifuged again, and resuspended om 15 ml. of 0.1 M potassium phosphate, pH 7.0. Cells were diluted into the same buffer to $OD_{550}$ equal to 0.8 and a final volume of 10 ml. To the PmKR1 cell suspension was added toluene to 1 mM final concentration. To the FM5/pKY287 cell suspension was added glucose to 0.2% final concentration and kanamycin to 50 μg/ml final concentration. Vials were capped and TCE added by syringe to a final concentration of 40 μM (5.2 ppm). Incubation was at 30° C. for 5-18 hours and the extent of TCE degradation was determined by gas chromatography.

After the TCE was degraded, cells were centrifuged for 5 minutes and supernatants passed through a 0.2μ filter. Chloride ion concentrations in supernatants were determined on an Orion EA 920 ion meter, using a model 94-17B chloride electrode and a model 90-02 reference electrode, both from Orion. A calibration curve from 20 μM KCl to 200 μM KCl in 0.1 M potassium phosphate, pH 7.0, was established by adding aliquots of KCl to a background control sample (PmKR1 or FM5/pKY287 cells in 0.1 M KPO$_4$ without any TCE added). Chloride ion concentrations in samples containing TCE were determined from this curve.

The results showed that 2.5 moles of chloride ion were released per mole of TCE using induced PmKR1 cells and 2.7 moles of chloride ion were released per mole of TCE using induced FM5 cells containing pKY287.

EXAMPLE 9

TCE Degradative Ability and Toluene Monooxygenase Activity

A. Toluene Monooxygenase Assay at High Cell Densities and Correlation with TCE Degradation For these assays, cells were grown in PAS medium containing 0.4% glutamate or in L broth to saturation. The FM5 cells, however, were grown as described in Example 6, except that the cells were induced at 42° C. for 3 hours, then returned to 30° C. for 2 hours. The cells were resuspended into an appropriate volume of the same medium to an OD$_{660}$ of 3.0. An aliquot of the cells was used for the determination of total cell protein as described in Example 6. An aliquot of 0 5 ml of cells was mixed with 4 micromoles of p-cresol in 10 μl and 15 nmoles of radioactive toluene (toluene-ring-$^{14}$C, Sigma Chemical Co., 56.3 mCi/nmole) in 5 μl and the mixture was incubated at room temperature with occasional vortexing for 20 minutes. After incubation, 20 μl of the mixture were spotted on a small piece of a thin-layer chromatography plate and the plate was air-dried for twenty minutes. The nonvolatile radioactivity remaining on the filter was determined in a liquid scintillation counter and was used to calculate the amount of toluene degradation product on the plate and the specific activity of toluene monooxygenase.

Table 7 summarizes the results of the above described assay at high cell density for a variety of strains that were also tested for TCE degradative ability. Table 7 also indicates the correlation of TCE degradative ability with toluene monooxygenase (TMO) activity. In particular. Table 7 demonstrates that under conditions of high cell density, the HB101 cells containing pMY402, and the FM5 cells containing pKY287, show levels of PmKR1 toluene monooxygenase enzyme activity approximately 2 to 4 times higher than that of wildtype PmKR1 cells. These same two genetically engineered host cells show superior abilities to degrade TCE as evidenced by a more sustained rate of degradation and an increased amount of degradation at higher TCE concentrations relative to wildtype PmKR1 cells.

Figure 7:
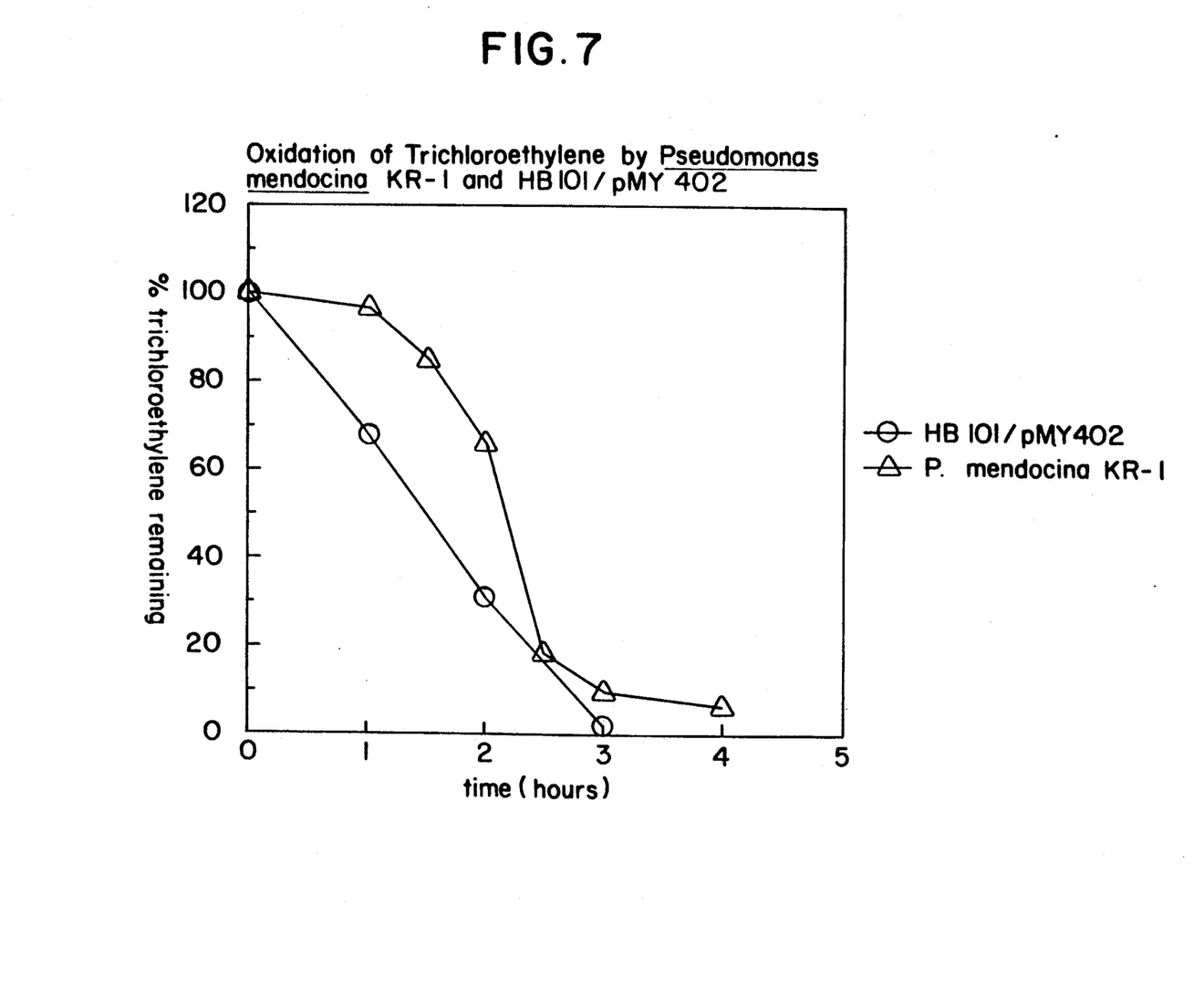
FIG. 7 is a graph showing the disappearance of 20 $\mu$M (2 6 ppm) TCE added to cells due to the metabolism of TCE into non-volatile material as a function of time, so as to compare the rate and extent of TCE degradation by wildtype PmKR1 cells and by HB101 cells containing the pMY402 recombinant plasmid (HB101/pMY402).
Figure 8:
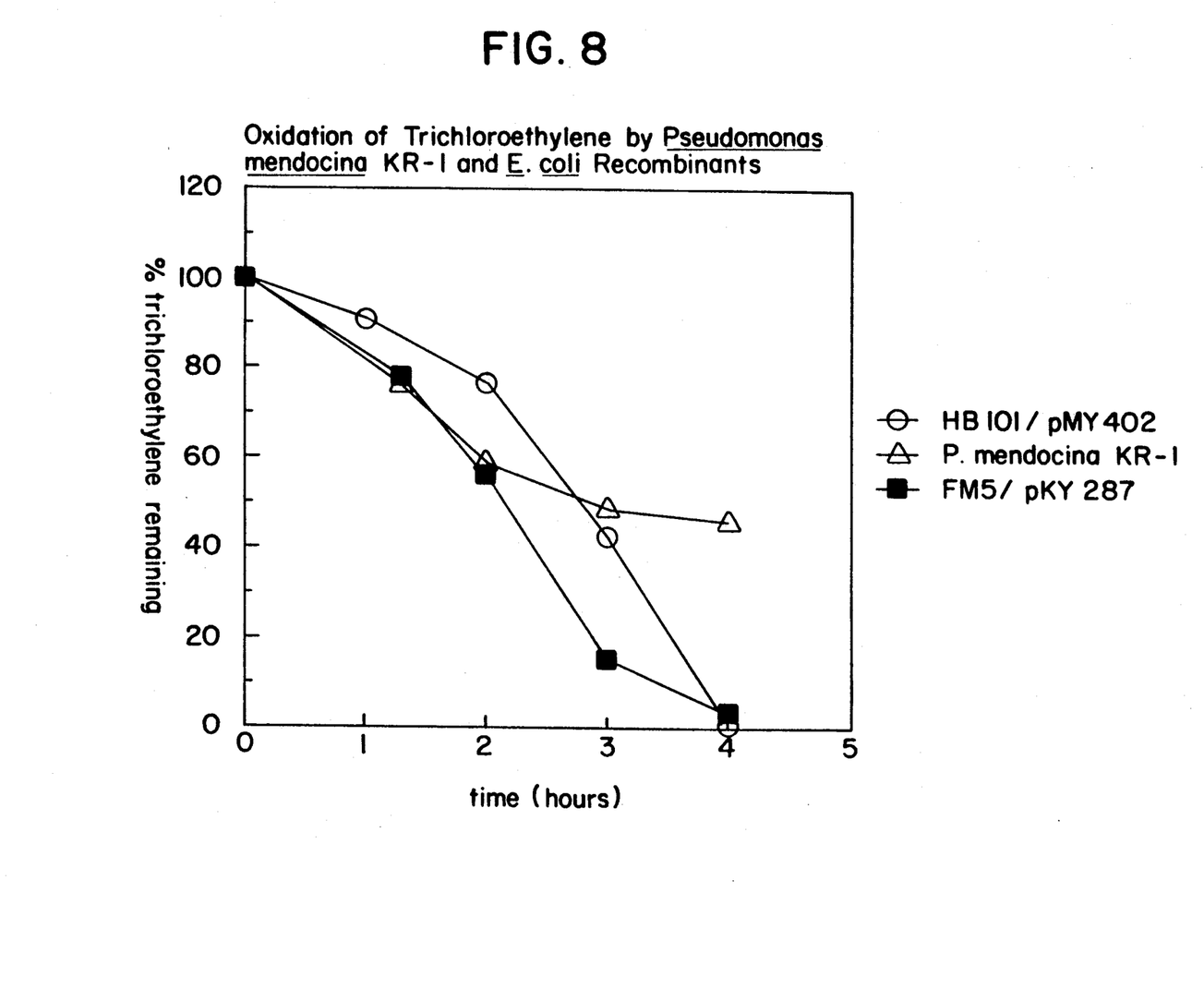
FIG. 8 is a graph similar to FIG. 7 but in which 50 $\mu$M (6.5 ppm) TCE was used instead of 20 $\mu$M (2.6 ppm) TCE as in FIG. 7. In addition, it includes results with E. coli FM5 cells containing recombinant plasmid pKY287 (FM5/pKY287), so as to compare the rate and extent of TCE degradation by wildtype PmKR1, HB101/pMY402 and FM5/pKY287 cells.

This is illustrated in FIGS. 7 and 8 for HB101 cells containing pMY402 induced with IPTG (open circles) as compared with wildtype PmKR1 cells (open triangles) and shown in addition in FIG. 8 for FM5/pKY287 cells (closed squares). Increased enzyme activity under the above-described conditions thus correlates with increased ability to degrade TCE as illustrated by FIG. 8 and Table 7.

TABLE 7

TCE Degradation and Toluene Monooxygenase Activity at High Cell Densities

| PLASMID | IN-DUCER | HOST | Units of TMO Activity* | Vector | TCE Degradation |
|---|---|---|---|---|---|
| pAUT1 | Toluene | PmKR1 | 0.130 | — | + |
| pAUT1 | None | PmKR1 | 0.010 | — | — |
| pMY402 | None | E. coli HB101 | 0.005 | pMMB66EH | — |
| pMY402 | IPTG | E. coli HB101 | 0.200 | pMMB66EH | + |
| pKY287 | Temp | E. coli FM5 | 0.500 | pCFM1146 | + |
| pCFM1146 | Temp | E. coli FM5 | 0.005 | — | — |
| pMMB66EH | IPTG | E. coli HB101 | 0.005 | — | — |

*One unit of TMO activity is expressed as 1 nmole of $^{14}$C toluene converted to nonvolatile material per minute per milligram of whole cell protein.

In addition to those plasmids listed in Table 7 containing PmKR1 toluene monooxygenase genes, other plasmids containing these genes including pKY277, pKY280, pKY281, pKY282, pMY401, pMY404 as described in U.S. patent application Ser. No. 177,631, (filed Apr. 5, 1988 and incorporated by reference) would be suitable for TCE degradation.

B. Toluene Monooxygenase Assay at Lower Cell Densities and Correlation with TCE Degradation Cells were grown as described in Example 6. The cell cultures were centrifuged and resuspended in PAS medium or PAS medium containing 0.2% glucose to an OD$_{550}$ of 0.5. The toluene monooxygenase assay was performed as described in part A above, except that the time of incubation with the $^{14}$C-toluene was 5 minutes, not 20 minutes.

Table 8 summarizes the results of the above described assay at lower cell densities for strains that were also tested for TCE degradative ability. Table 8 also indicates the correlation of TCE degradative ability with toluene monooxygenase (TMO) activity. In contrast to the results obtained at higher cell densities as shown in Table 7, Table 8 demonstrates that under conditions of lower cell density, the HB101 cells containing pMY402, and the FM5 cells containing pKY287, show levels of PmKR1 toluene monooxygenase enzyme activity lower than that of wildtype PmKR1 cells.

TABLE 8

TCE Degradation and Toluene Monooxygenase Activity at Lower Cell Densities

| PLASMID | IN-DUCER | HOST | Units of TMO Activity* | Vector | TCE Degradation |
|---|---|---|---|---|---|
| pAUT1 | Toluene | PmKR1 | 8.35 | — | + |
| pAUT1 | None | PmKR1 | 0.08 | — | — |
| pMY402 | None | E. coli HB101 | 0.01 | pMMB66EH | — |

TABLE 8-continued

TCE Degradation and Toluene Monooxygenase Activity at Lower Cell Densities

| PLASMID | IN-DUCER | HOST | Units of TMO Activity* | Vector | TCE Degradation |
|---|---|---|---|---|---|
| pMY402 | IPTG | E. coli HB101 | 0.72 | pMMB66EH | + |
| pKY287 | Temp | E. coli FM5 | 1.29 | pCFM1146 | + |
| pKY287 | None | E. coli FM5 | 0.12 | pCFM1146 | − |
| pCFM1146 | Temp | E. coli FM5 | 0.05 | — | — |
| pMMB66EH | IPTG | E. coli HB101 | <0.01 | — | — |

*One unit of TMO activity is expressed as 1 nmole of $^{14}C$ toluene converted to nonvolatile material per minute per milligram of whole cell protein.

By genetically engineering the PmKR1 toluene monooxygenase genes so as to place them under the control of various promoters, increased levels of expression of PmKR1 toluene monooxygenase gene products have been achieved with a concomitant increase in TCE degradative ability.

Under conditions where PmKR1 cells are incubated with at least a 40 fold excess of toluene over TCE, a lag time of several hours has been observed before the PmKR1 cells begin degrading TCE (FIG. 7, open triangles). This is because toluene and TCE are cosubstrates for PmKR1 toluene monooxygenase and both are in competition for the available PmKR1 toluene monooxygenase enzymes. Therefore, when toluene and TCE are simultaneously present and toluene is present in excess concentrations as compared with TCE, PmKR1 cells will begin degrading TCE only after the toluene concentration has been considerably reduced. This same lag period is not seen when PmKR1 cells are first induced with toluene, and then the toluene is removed before adding TCE (FIG. 2). By cloning the PmKR1 toluene monooxygenase genes and placing them under the control of promoters not induced by toluene, the cosubstrate problem just described has been eliminated.

It is expected that many other promoter systems other than the toluene-inducible, IPTG-inducible and temperature-inducible promoters described herein will be appropriate for increased toluene monooxygenase expression and thus increased TCE degradation. Moreover, it is expected that many other types of plasmid vectors and microorganism host cells will be suitable for PmKR1 toluene monooxygenase expression and TCE degradation. As such, the invention should not be limited by the illustrative embodiments described above. Instead, the invention is to be judged by the claims which follow.

What is claimed is:

1. A method for the microbial degradation of trichloroethylene comprising treating trichloroethylene with *Pseudomonas mendocina* KR-1 cells, the cells having been treated with an inducer of toluene monooxygenase genes.

2. A method for the microbial degradation of trichloroethylene comprising treating trichloroethylene with *Pseudomonas putida* Y2101 cells, the cells having been treated with an inducer of toluene monooxygenase genes.

3. A method for the microbial degradation of trichloroethylene comprising treating trichloroethylene with a microorganism host cell containing a recombinant plasmid, the recombinant plasmid containing toluene monooxygenase genes from *Pseudomonas mendocina* KR-1, the microorganism host cell containing the recombinant plasmid having been treated with an inducer of the toluene monooxygenase genes.

4. A method according to claim 3 wherein the recombinant plasmid comprises pKY277, pKY280, pKY281 or pKY282 and the inducer is toluene.

5. A method according to claim 3 wherein the recombinant plasmid is pMY402, pMY405, pMY401 or pMY404 and the inducer is isopropyl-β-D-thiogalactopyranoside.

6. A method according to claim 3 wherein the recombinant plasmid is pKY287 and the inducer is a temperature shift up to 42° C.

7. A method according to claim 3 wherein the microorganism host cell comprises *E. coli* JM109, JM83, HB101 or FM5.

8. A method for microbial degradation of trichloroethylene chemical waste comprising the steps of:
applying to a locus of trichloroethylene contamination a microorganism host cell containing a recombinant plasmid, the recombinant plasmid containing toluene monooxygenase genes from *Pseudomonas mendocina* KR-1 capable of degrading the trichloroethylene in the presence of an inducer of the toluene monooxygenase genes, and
monitoring the degradation of the trichloroethylene contamination at the locus of application.

9. A method according to claim 8 wherein the locus of trichloroethylene contamination to be degraded is groundwater, drinking water or waste water containing trichloroethylene chemical waste.

10. A method according to claim 8 wherein the locus of trichloroethylene contamination to be degraded is a landfill or a leachate removed from a landfill containing trichloroethylene chemical waste.

11. A method according to claim 8 wherein the locus of trichloroethylene contamination to be degraded is soil containing trichloroethylene chemical waste.

12. A method according to claim 8 wherein the recombinant plasmid comprises pKY277, pKY280, pKY281 or pKY282 and the inducer is toluene.

13. A method according to claim 8 wherein the recombinant plasmid is pMY402, pMY405, pMY401 or pMY404 and the inducer is isopropyl-β-D-thiogalactopyranoside.

14. A method according to claim 8 wherein the recombinant plasmid is pKY287 and the inducer is a temperature shift up to 42° C.

15. A method according to claim 7 wherein the microorganism host cell comprises *E. coli* JM109, JM83, HB101 or FM5.

* * * * *